US007427619B2

(12) United States Patent
Burzynski

(10) Patent No.: US 7,427,619 B2
(45) Date of Patent: Sep. 23, 2008

(54) FORMULATION OF AMINO ACIDS AND RIBOFLAVIN USEFUL TO REDUCE TOXIC EFFECTS OF CYTOTOXIC CHEMOTHERAPY

(76) Inventor: Stanislaw R. Burzynski, 20 W. Rivercrest, Houston, TX (US) 77042

( * ) Notice: Subject to any disclaimer, the term of this patent is extended or adjusted under 35 U.S.C. 154(b) by 304 days.

(21) Appl. No.: 11/108,277

(22) Filed: Apr. 18, 2005

(65) Prior Publication Data
US 2005/0182064 A1    Aug. 18, 2005

Related U.S. Application Data

(63) Continuation-in-part of application No. 09/995,010, filed on Nov. 27, 2001, now abandoned.

(51) Int. Cl.
| A61K 31/525 | (2006.01) |
| A61K 31/415 | (2006.01) |
| A61K 31/40 | (2006.01) |
| A61K 31/205 | (2006.01) |
| A61K 31/19 | (2006.01) |
| A61K 31/195 | (2006.01) |

(52) U.S. Cl. .................. 514/251; 514/400; 514/419; 514/423; 514/556; 514/557; 514/561; 514/562

(58) Field of Classification Search ............... 514/251, 514/556, 557, 561, 562, 400, 419, 423
See application file for complete search history.

(56) References Cited

U.S. PATENT DOCUMENTS

| 4,826,680 A | 5/1989 | Jaeger ........................ 424/95 |
| 5,045,468 A | 9/1991 | Darfler ................. 435/240.31 |
| 5,430,064 A | 7/1995 | Hirsch et al. ................ 514/554 |
| 5,547,927 A | 8/1996 | Cope et al. ..................... 514/2 |
| 5,550,146 A | 8/1996 | Acosta et al. ............... 514/400 |
| 5,656,608 A | 8/1997 | Schneider et al. ............ 514/42 |
| 5,719,134 A | 2/1998 | Schmidl et al. ............... 514/58 |
| 5,776,913 A | 7/1998 | Ogilvie et al. ................ 514/57 |
| 5,817,695 A | 10/1998 | Pellico ....................... 514/558 |
| 6,337,094 B1 | 1/2002 | Guardiola et al. .......... 424/602 |

FOREIGN PATENT DOCUMENTS

| EP | 0 747 395 A1 | 12/1996 |
| GB | 2 029 220 | 3/1980 |

OTHER PUBLICATIONS

Kulcsár, G. "Inhibition of the Growth of a Murine and Various Human Tumor Cell Lines in Culture and in Mice by Mixture of Certain Substances of the Circulatory System" *Cancer Biotherapy*, 10: 157-176 (1995).
Cascino, A., et al. "Plasma Amino-Acids in Human Cancer: the Individual Role of Tumour, Malnutrition and Glucose Tolerance" *Clinical Nutrition*, 7: 213-218 (1988).
Cole, N., et al. "Character of Terminal Illness in the Advanced Cancer Patient: Pain and Other Symptoms During the Last Four Weeks of Life" *J. Pain Symptom Management*, 5: 83-93 (1990).
McGeer, A.J., et al. "Parenteral Nutrition in Patient Receiving Cancer Chemotherapy" *Annals of Internal Medicine*, 110: 734-736 (1989).
Koretz, R.L. "Parental Nutrition: Is It Oncologically Logical?" *J. Clinical Oncology*, 2: 534-538 (1984).
Breitbart, W., et al. "Pemoline: An Alternative Psychostimulant for the Management of Depressive Disorders in Cancer Patients" *Psychosomatics*, 33: 352-356 (1992).
Baron, P.L., et al. "Effects of Parenteral Nutritional on Cell Cycle Kinetics of Head and Neck Cancer" *Arch. Surgery*, 121: 1282-1286 (1986).
Reynolds, J.V., et al. "Immunologic Efects of Arginine Supplementation in Tumor-Bearing and Non-Tumor-Bearing Hosts" *Ann. Surgery*, 211: 202-210 (1990).
Reynolds, J.V., et al. "Argine, Protein Malnutrition, and Cancer" *J. Surgical Res.*, 45: 513-522 (1988).
Barbul, A. "Arginine: Biochemistry, Physiology, and Therapeutic Implications" *J. Parenteral Enteral Nutrition*, 10: 227-238 (1986).
Tachibana, K., et al. "Evaluation of the Effects of Arginine-Enriched Amino Acid Solution on Tumor Growth" *J. Parenteral Enteral Nutrition*, 9: 428-434 (1985).
Heyland, D.K., et al. "Total Parenteral Nutrition in the Critically Ill Patient: A Meta-Analysis" *J. Am. Med. Assoc.*, 280: 2013-2019 (1998).
Vachon, M.L.S., et al. "Psychosocial Issues Palliative Care: the Patient, the Family, and the Process and Outcome of Care" *J. pain Symptom Management*, 10: 142-150 (1995).
Braga, M., et al. "Perioperative Immunonutrition in Patients Undergoing Cancer Surgery" *Arch. Surgery*, 134: 428-433 (1999).
Cozzaglio, L., et al. "Does Parenteral Nutrition Increase Tumor Growth? A Review" *Tumori*, 80: 169-174 (1994).
Muscaritoli, M., et al. "Plasma Amino Acid Concentrations in Patients with Acute Myelogenous Leukemia" *Nutrition*, 15: 195-199 (1999).
Wheeler, M.D., et al. "Glycine: A New Anti-Inflammatory Immunonutrient" *Cell. Mol. Life Sciences*, 56: 843-856 (1999).
Redmond, H.P., et al. "Immunonutrition: The Role of Taurine" *Nutrition*, 14: 599-604 (1998).
Rivlin, R.S. "Riboflavin and Cancer: A Review" *Cancer Research*, 33: 1977-1986 (1973).
Rivlin, R.S., et al. "Effects of Riboflavin Deficiency Upon Concentrations of Riboflavin, Flavin Mononucleotide, and Flavin Adenine Dinucleotide in Novikoff Hepatoma in Rats" *Cancer Research*, 33: 3019-1023 (1973).

(Continued)

*Primary Examiner*—Kevin E Weddington
(74) *Attorney, Agent, or Firm*—Howrey LLP

(57) ABSTRACT

Pharmaceutical compositions effective in alleviating or reducing the effects of fatigue and weakness associated with cancer and cancer chemotherapy are disclosed. The pharmaceutical compositions of the present invention comprise riboflavin, effectors of the urea cycle in free form or pharmacologically acceptable salts thereof, and amino acids selected from the groups of essential and non-essential amino acids, in free form or pharmaceutically acceptable salts thereof, suitably combined with appropriate carriers, diluents, or excipients. Also disclosed are methods of alleviating or reducing the effects of fatigue and weakness associated with cancer and cancer chemotherapy by administration of pharmaceutical compositions of the present invention.

10 Claims, No Drawings

OTHER PUBLICATIONS

Rivlin, R.S. "Riboflavin" *Adv. Exp. Med. Biol.* 206: 349-355 (1986).

Chaudhry, M., et al. "The Vitamin D3 analog, ILX-23-7553, Enhances the Response to Adriamycin and Irradiation in MCF-7 Breast Tumor Cells." *Cancer Chemother, Pharmacol.* 47: 429-436 (2001).

Liau, M.C., et al. "Riboflavin as a Minor Active Anticancer Component of Antieoplaston A2 and A5" *Int. J. Tissue Reac.* 12: 19-?? (1990).

Wargovich, M. J., et al. "Efficacy of potential chemopreventive agents on rat colon aberrant crypt formation and progression" *Carcinogenesis*, 21: 1149-1155, (2000).

Wersinger, C., et al. "Detailed study of the different taurine uptake systems of colon LoVo MDR and non-MDR cell lines" *Amino Acids*, 19: 667-685 (2000).

Grossie, V. B., Jr., et al. "Substituting Ornithine for Arginine in Total Parenteral Nutrition eliminates Enhanced Tumor Growth" *J. of Surgical Oncology*, 50: 161-167, (1992).

Grossie, V. B., Jr., et al. "A Parenteral Nutrition Regimen With Ornithine Substituted for Arginine Alter the Amino Acid, bu Not Polyamine, Content of the Ward Colon Tumor" *Nutrition and Cancer*, 27: 102-106 (1997).

Bruera, E. et al. "Psychstimulants as Adjuvant Analegesics" *Journal of Pain and Symptom Management*, 9: 412-415 (1994).

Chance, et al., "Reduction of Tumor Growth Following Treatment with a Glutamine Antimetabolite" *Life Sciences* 42(1) (1988) 87-94 (abstract).

Synold, et al., "Role of Folypolyglutamate Synthetase (FPGS) in Antifolate Chemotherapy; a Biochemical and Clinical Update", *Leukemia & Lymphoma* 21 (1-2) (1996) 9-15 (abstract).

Ronald R. Koertz, "Parental Nutrition: Is it Oncologically Logical?" *Journal of Clinical Oncology*, vol. 2, No. 5, may 1984, pp. 534-538.

Copeland J.A. et al., "Inhibition of Estrogen Stimulated Mitogenesis by 3-Phenylacetylamino-2,6-Piperdinedione and its Para-Hydroxy Analog", *Journal of Steroid Biochemistry and Molecualr Biology*, 46(4):451-462 (1993) (abstract).

Burzynski, S.R. et al., "Toxicology Studies on Oral Formulation of Antineoplaston A10 in Cancer patients", *Drugs Under Experiments and Clinical Research*, 10:611-619 (1984) (abstract).

FORMULATION OF AMINO ACIDS AND RIBOFLAVIN USEFUL TO REDUCE TOXIC EFFECTS OF CYTOTOXIC CHEMOTHERAPY

CROSS-REFERENCE TO RELATED APPLICATION

This is a Continuation-in-Part application claiming priority to U.S. non-provisional application Ser. No. 09/995,010, filed Nov. 27, 2001 now abandoned.

BACKGROUND OF THE INVENTION

1. Field of the Invention

The present invention relates generally to the fields of pharmaceutical chemistry and formulation. More particularly, it concerns the use of an effective amount of riboflavin and amino acids, in any combination, in the alleviation of the nutritional, metabolic and toxic symptoms of cancer and cancer chemotherapy in diagnosed cancer patients.

2. Description of the Related Art

In spite of the progress which has been made over the years in the areas of cytotoxic chemotherapy, immunotherapy, and radiation therapy in the treatment of patients with a variety of malignant and nonmalignant disorders, most of the commonly used antineoplastic drugs produce immediate toxicities in the organs composed of self-renewing cell populations such as the gastrointestinal tract epithelium. As a result, many patients suffer such toxic effects as pancytopenia, alopecia, nausea and vomiting, as well as a variety of other physical distresses. In fact, it has been shown in numerous studies (Vachon, M. L. S. et al., *J. Pain Symptom Management*, 10, 142-150 (1995); Coyle, N. et al., *J. Pain Symptom Management*, 5, 83-93 (1990)) that outside of pain, the most common symptoms reported by patients diagnosed with cancer and/or undergoing chemotherapy treatment for cancer are fatigue, weakness, and appetite disturbances, the latter of which directly contributes to the other symptoms.

Moreover, these symptoms are so common that they are frequently neglected by physicians, and patients may be told that there is nothing that can be done to remedy these side-effects. In some patients, correction of anemia, reduced concentrations of sodium, potassium, calcium, and glucose in the blood, dehydration, and enhanced function of major organs may provide a relief. Adjustment of the dosages of medications, which may contribute to fatigue and weakness, including analgesics, muscle relaxants, and anti-depressants may also provide temporary relief. Pharmacological management of fatigue includes the use of psychostimulatory agents such as methylphenidate, pemoline and corticosteroids, as described by Brietbart, W. et al. (*Psychosomatics*, 33, 352-356 (1992)) Unfortunately, in most patients such measures are short-lasting or not effective.

When total parenteral nutrition (TPN) was introduced, it was speculated that improvement of the patient's nutrition would treat several emergency situations related to cancer and the side effects of therapy, as well as reduce weakness and tiredness. Unfortunately, this was not observed in most cancer patients receiving TPN, and the efficacy of TPN to improve patient nutritional status and survival remains questionable (Koretz, R. L. *J. Clinical Oncology*, 2: 534-538 (1984); McGeer, A. J.; Detsky, A. S.; O'Rourke, K. *Ann. Internal Med.*, 110: 734-736 (1989)). A variety of studies have been conducted since the inception of TPN, with an array of conflicting reports. In some of them, TPN facilitated cancer progression through supply of large quantities of nutrients necessary for cancer growth, suggesting that the broad use of TPN in cancer patients could be deleterious at worst or ineffective at best. While it has been clearly shown that exogenous substrates have a distinct effect on both host and cancer metabolism, the characteristics of the substrates, such as caloric intake and the kind of amino acids used appear to be crucial for a selective response. As a result, fatigue and weakness are currently not indicators for the use of TPN in cancer patients.

In spite of such seemingly conflicting reports, several amino acids have indicated promise as nutritional supplements in the treatment of a variety of disorders, including cancer. Key amongst these are arginine, glycine, ornithine and taurine. The amino acid arginine has properties which suggest that it may be of value both nutritionally and immunologically when administered as a dietary supplement. In fact, research has shown that a retardation in tumor growth, tumor regression, decreased tumor incidence, or a combination of all three can be affected by the administration of dietary arginine. Additionally, mixtures which contain arginine as well as a variety of other amino acids, sugars, vitamins, and nucleobases have exhibited potentially cytotoxic effects against several cancer cell lines. The non-essential amino-acid glycine has been shown to inhibit hepatocyte proliferation, and may have general anticancer properties as a dietary supplement.

In addition to amino acids, a variety of vitamins and their analogs have been tested for potential cancer therapeutic effects as part of TPN regimens, but for the most part the results have been inadequate to confirm or deny the benefits, and the evidence relating to cancer is weak or conflicting. However, several vitamins, most notably Vitamins A, B, C, and D have shown preliminary promise for use in cancer therapy.

There accordingly exists a need for a process to alleviate the side effects of cytotoxicity associated with cancer and cancer chemotherapy, specifically a decrease of fatigue and weakness, an increase of energy, and the reduction of toxicity of chemotherapy regimens. Simultaneously, improving the nutritional status of cancer patients unlikely to have a curative response to existing therapeutic regimens has potential for decreasing the size of the tumors within the patient.

SUMMARY OF THE INVENTION

The present invention provides a method for alleviation or reduction of cancer chemotherapy toxicity, involving administering to a patient with a pharmaceutical composition comprising therapeutically-effective amounts of riboflavin, a component of the urea cycle, and effective amounts of the amino acids alanine, glycine, serine, taurine, threonine, and valine.

It is thus an object of the invention to provide a method for treatment of fatigue and weakness by administering to a subject with a composition comprising riboflavin, an effector of the urea cycle, and one or more amino acids.

A further aspect of the present invention is to provide a pharmaceutically acceptable agent for the alleviation of the symptoms of fatigue and weakness associated with cancer and cancer chemotherapy cytotoxicity, comprising a therapeutically effective amount of riboflavin, an effector of the urea cycle, and one or more amino acids selected from a group of essential and non-essential amino acids, wherein the latter two constituents are in free form or pharmacologically acceptable salts. A preferred composition consists of the six amino acids, alanine, glycine, serine, taurine, threonine, and valine; an effector of the urea cycle selected from L-arginine, L-ornithine, and L-citrulline; riboflavin; and a pharmaceutically acceptable diluent. A particularly preferred pharmaceutical composition of the present invention comprises riboflavin; an effector of the urea cycle selected from the group consisting of arginine, ornithine, citrulline, and mixture thereof; the amino acids alanine, glycine, serine, taurine, threonine, and valine; and a suitable solvent, diluent, excipient, or carrier, wherein the concentration of riboflavin is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL. The composition is is devoid of the amino acids, glutamine, leucine, and tryptophan.

A still further aspect of the present invention is to provide a pharmaceutically acceptable agent for the alleviation of the symptoms of fatigue and weakness associated with cancer and cancer chemotherapy cytotoxicity, comprising a therapeutically effective amount of riboflavin, an effector of the urea cycle, and one or more amino acids selected from a group of essential and non-essential amino acids, and 3-phenylacetylamino-2,6-piperidinedione or one or more of the compounds, phenylacetylglutamine, phenylacetylisoglutamine, or phenylbutyrate.

These and other objects will be more readily understood upon consideration of the following detailed descriptions of embodiments of the invention.

DETAILED DESCRIPTION OF PREFERRED EMBODIMENTS

The invention is described below in terms of the preferred embodiments known at the time of filing of this application. These embodiments represent the best mode presently contemplated by the inventor for preparing the pharmaceutical compositions and their method of use.

A. Preparation of Pharmaceutical Compositions

Riboflavin, used within the present invention, can be obtained from a commercial source (e.g., Spectrum Laboratory Products, Inc., Gardena, Calif.) or can be prepared synthetically by any known technique in the art, e.g. by condensation of a ribitylxylidine azo derivative with barbituric acid (Yoneda, F. et al., J. Chem. Soc., Perkin Trans. I, 348 (1978); U.S. Pat. No. 2,807,611). For pharmaceutical use, riboflavin is preferably obtained from a fermentation process of any number of bacteria, or through a combination of synthetic and biotechnology techniques described in the art (U.S. Pat. Nos. 6,150,364; 5,589,355).

Similarly, the amino acids used within the present invention can be obtained from a commercial source (e.g., Kyowa Hakko Kogyo Co., LTD., Tokyo, Japan), by fermentation methods, or can be prepared synthetically using any number of techniques in the art, e.g. through the displacement reactions on .alpha.-halo acids. For pharmaceutical use, the amino acids are preferably prepared synthetically. The amino acids used within the present invention are all of the L-(levorotatory), stereochemical series and are all proteinogenic .alpha.-amino acids except for glycine, which does not have optic isomers and taurine, which is an beta.-amino acid and does not have optic iosomers.

The compounds of the present invention can also exist in different stereoisomeric forms by virtue of the presence of one or more asymmetric centers in the compound. The present invention contemplates L-stereoisomeric forms of the compounds, as well as mixtures thereof, including racemic mixtures. Individual stereoisomers may be obtained commercially, or by methods known in the art, such as the separation of stereoisomers in chiral chromatographic columns.

Further, the compounds of the present invention can exist in unsolvated as well as solvated forms with pharmaceutically-acceptable solvents such as water, ethanol, and the like. In general, solvated forms of the compounds are considered to be equivalent to the unsolvated forms for the purposes of the present invention.

The use of the term "pharmaceutically-acceptable salts" means salts which have the biological activity of the parent compound while lacking any toxic activity at the selected administration level. Determination of whether a salt is pharmaceutically-acceptable salt can be determined readily by methods known to those of skill in the art. Pharmaceutically acceptable salts include, but are not limited to, organic diethanolamine, cyclohexylamine and amino acid salts, and inorganic sodium, potassium, and ammonium salts.

The term "amino acid of the invention", as used hereinafter, is meant to refer to glycine, alanine, serine, valine, threonine and/or taurine, in free amino acid form and/or pharmacologically acceptable salt form.

As used herein, the term "urea cycle effector" includes any of the amino acids comprising the urea cycle wherein such a cycle serves as a metabolic pathway for disposing of cellular breakdown products containing nitrogen. Such effectors are selected from the group comprising arginine, ornithine, and citrulline.

As used herein, the term "patient" refers to human patients.

The term "unit dosage form", or alternatively "unit dosage levels" as used herein refers to physically discrete units suitable as unitary dosages for human subjects, each unit containing a predetermined quantity of active material calculated to produce the desired therapeutic effect in association with the required pharmaceutical diluent, carrier, or vehicle. The specifications for the novel unit dosage forms of this invention are dictated by and are directly dependent upon (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accordance with this invention are tablets, capsules, troches, powder packets, wafers, cachets, teaspoonfuls, tablespoonfuls, dropperfuls, ampules, vials, I.V. bags, segregated multiples of any of the foregoing, and other forms as described herein.

The present invention therefore provides the use of the amino acid(s) of the invention, namely alanine, glycine, serine, taurine, threonine and valine, in combination with riboflavin and an effector of the urea cycle in minimizing the effects of fatigue and weakness in cancer patients resulting from cancer and cancer chemotherapy toxicity; compositions containing the amino acids of the invention in combination with riboflavin and an effector of the urea cycle; the use of the composition of the invention in the manufacture of compositions for minimizing and alleviating the effects of fatigue and weakness in cancer patients resulting from cancer and cancer chemotherapy toxicity; and a method of minimizing and alleviating the effects of fatigue and weakness in cancer patients resulting from cancer and cancer chemotherapy cytotoxicity. Typical compositions contain the selected effector of urea cycle (L-arginine, L-ornithine or L-citrulline) in an amount from about 50 to about 3000 times the molar concentration of riboflavin. Further, each of the amino acids is generally provided in a molar amount from about 0.1 to about 3.0 of the selected effector of the urea cycle. The inventive composition is devoid of the amino acids, glutamine, leucine, and tryptophan. The amino acids glutamine, leucine, and tryptophan are avoided in the composition since they each may contribute to promote tumor growth. The composition is further devoid of protein matter. If protein were present it might hydrolyze and contribute to the presence of unwanted amino acids glutamine, leucine, and tryptophan.

One embodiment of the present invention (AVA) is particularly well suited for patients who have normal kidney function. An alternative embodiment of the present invention (AVB) is particularly well suited for those patients who have kidney insufficiency or urological abnormalities. These formulations were initially used for patients who require additional parenteral nutrition. It was observed that even after a few days of administration, many patients had experienced an increased energy level and a decrease in fatigue and weakness. The patients were also able to tolerate standard cytotoxic chemotherapy without significant side effects. Since this time, both formulations AVA and AVB have been used. Typical formulations are shown below.

| AVA | | AVB | |
|---|---|---|---|
| Component | Amount (g/L) | Component | Amount (g/L) |
| L-Alanine | 4.46 | L-Alanine | 4.46 |
| Glycine | 5.25 | Glycine | 5.25 |
| L-Serine | 5.25 | L-Serine | 5.25 |
| Taurine | 1.88 | Taurine | 1.88 |
| L-Threonine | 5.96 | L-Threonine | 5.96 |
| L-Valine | 3.51 | L-Valine | 3.87 |
| L-Arginine | 8.71 | L-Ornithine | 8.43 |
| Riboflavin ($B_2$) | 0.05 | Riboflavin ($B_2$) | 0.05 |

To prepare a pharmaceutical composition of solution AVA according to the present invention, an aqueous solution of L-arginine and riboflavin in about a 500:1 molar ratio is prepared such that the concentration of L-arginine in solution is about 2 mg/mL to about 120 mg/mL. The solution also contains the amino acids L-alanine, L-serine, and L-threonine in a 1:1 molar ratio with L-arginine in a concentration of about 1 mg/mL to about 90 mg/mL; the amino acid glycine in a 1.4:1 molar ratio with L-arginine in a concentration of about 1 mg/mL to about 75 mg/mL; the beta-amino acid taurine in a 0.3:1 molar ratio with L-arginine in a concentration of about 0.5 mg/mL to about 30 mg/mL; and the amino acid L-valine in a 0.6:1 molar ratio with L-arginine in a concentration of about 1 mg/mL to about 50 mg/mL. Preparation of the AVA solution can be performed using any technique known to those skilled in the art. It is to be noted that the solution is to be made sterile, and the pH is to be adjusted to a value at or near the physiological pH of 7.4, e.g. 6.8, using sodium hydroxide and hydrochloric acid as needed.

To prepare a pharmaceutical composition of solution AVB according to the present invention, an aqueous solution of L-ornithine and riboflavin in about a 500:1 molar ratio is prepared such that the concentration of L-ornithine in solution is about 2 mg/mL to about 120 mg/mL. The solution also contains the amino acids L-alanine, L-serine, and L-threonine in a 1:1 molar ratio with L-ornithine in a concentration of about 1 mg/mL to about 90 mg/mL; the amino acid glycine in a 1.4:1 molar ratio with L-ornithine in a concentration of about 1 mg/mL to about 75 mg/mL; the beta-amino acid taurine in a 0.3:1 molar ratio with L-ornithine in a concentration of about 0.5 mg/mL to about 30 mg/mL; and the amino acid L-valine in a 0.7:1 molar ratio with L-ornithine in a concentration of about 1 mg/mL to about 50 mg/mL. Preparation of the AVB solution can be performed using any technique known to those skilled in the art. It is to be noted that the solution is to be made sterile, and the pH is to be adjusted to a value at or near the physiological pH of 7.4, e.g. 6.8, using sodium hydroxide and hydrochloric acid as needed.

An alternative embodiment of the present invention (AVC) is useful for the prevention of breast, lung and liver cancers as well as for reducing the toxic effects of cytotoxic chemotherapy. A pharmaceutical composition AVC according to the present invention typically comprises 0.01-10 wt % riboflavin, 1-15 wt % arginine, and 1-15 wt % ornithine, 1-15 wt % alanine, 1-15 wt % glycine, 1-15 wt % serine, 1-15 wt % threonine 1-15 wt % valine, and 25-75 wt % 3-phenylacetylamino-2,6-piperidinedione. A typical AVC formulation is shown below.

| AVC | |
|---|---|
| Component | % Composition |
| L-Alanine | 7.0 |
| Glycine | 7.0 |
| L-Serine | 7.0 |
| Taurine | 0.00 |
| L-Threonine | 7.0 |
| L-Valine | 7.0 |
| L-Arginine | 7.6 |
| L-Ornithine | 7.0 |
| Riboflavin ($B_2$) | 1.4 |
| 3-phenylacetylamino-2,6-piperidinedione | 49.0 |

An alternative embodiment of the present invention (AVD) comprises 0.01-10 wt % riboflavin, 1-15 wt % arginine, and 1-15 wt % ornithine, 1-15 wt % alanine, 1-15 wt % glycine, 1-15 wt % serine, 1-15 wt % threonine 1-15 wt % valine, and 25-75 wt % phenylacetylglutamine (PG). Phenylacetylglutamine is a metabolite of 3-phenylacetylamino-2,6-piperidinedione which is formed during partial enzymatic digestion in small intestine. Phenylacetylglutamine is a derivative of glutamine. A typical AVD formulation is shown below.

| AVD | |
|---|---|
| Component | % Composition |
| L-Alanine | 7.0 |
| Glycine | 7.0 |
| L-Serine | 7.0 |
| Taurine | 0.00 |
| L-Threonine | 7.0 |
| L-Valine | 7.0 |
| L-Arginine | 7.6 |
| L-Ornithine | 7.0 |
| Riboflavin ($B_2$) | 1.4 |
| Phenylacetylglutamine (PG) | 49.0 |

Another alternative embodiment of the present invention (AVE) comprises 0.01-10 wt % riboflavin, 1-15 wt % arginine, and 1-15 wt % ornithine, 1-15 wt % alanine, 1-15 wt % glycine, 1-15 wt % serine, 1-15 wt % threonine 1-15 wt % valine, and 25-75 wt % phenylacetylisoglutamine (isoPG). Phenylacetylisoglutamine is a metabolite of 3-phenylacetylamino-2,6-piperi-dinedione which is formed during partial enzymatic digestion in small intestine. Phenylacetylisoglutamine is a derivative of glutamine. A typical AVE formulation is shown below.

AVE

| Component | % Composition |
| --- | --- |
| L. Alanine | 7.0 |
| Glycine | 7.0 |
| L-Serine | 7.0 |
| Taurine | 0.00 |
| L-Threonine | 7.0 |
| L-Valine | 7.0 |
| L-Arginine | 7.6 |
| L-Ornithine | 7.0 |
| Riboflavin ($B_2$) | 1.4 |
| Phenylacetylisoglutamine (isoPG) | 49.0 |

Still another alternative embodiment of the present invention (AVF) comprises 0.01-10 wt % riboflavin, 1-15 wt % arginine, and 1-15 wt % ornithine, 1-15 wt % alanine, 1-15 wt % glycine, 1-15 wt % serine, 1-15 wt % threonine 1-15 wt % valine, and 25-75 wt % sodium phenylbutyrate. Sodium phenylbutyrate converts to phenylacetylglutamine (PG) in the liver and is a pro drug of phenylacetylglutamine. A typical AVF formulation is shown below.

AVF

| Component | % Composition |
| --- | --- |
| L-Alanine | 7.0 |
| Glycine | 7.0 |
| L-Serine | 7.0 |
| Taurine | 0.00 |
| L-Threonine | 7.0 |
| L-Valine | 7.0 |
| L-Arginine | 7.6 |
| L-Ornithine | 7.0 |
| Riboflavin ($B_2$) | 1.4 |
| Sodium phenylbutyrate | 49.0 |

The sterile pharmaceutical compositions AVA, AVB, AVC, AVD, AVE and AVF should be stored at room temperature (15-30.degree. C.) without refrigeration or freezing. They should be stored in such a manner that they are protected from light until the time of usage.

The dosage administered of the present composition will be dependent upon a combination of the identity of the neoplastic disease; the type of host involved, including its age, health, and weight; the type of concurrent treatment, if any; the frequency of treatment and the therapeutic ratio.

Illustratively, typical daily dosage levels of the compounds of the present invention will be in the range of from about 7 mg/kg/d (low end) to about 4000 mg/kg/d. (high end) of host body weight. Preferred daily doses shall generally be in the range of 1000 mg/kg/d of host body weight. Dosages will depend upon method of administration.

The compositions of the present invention can be prepared for administration to humans in unit dosage forms by a variety of routes, including, but not limited to, oral, subcutaneous, bronchial, pharyngolaryngeal, intranasal and intravenous. Preferred method of administration of AVA and AVB is as intravenous solution. AVC is particularly suitable for formulation as a solid for encapsulation in gel caps. AVD, AVE, and AVF are preferably administered in oral dosage form. They, however, are also suitable for intravenous infusions. The total concentration of the ingredients for AVD, AVE and AVF can be as high as 300 mg/mL.

The pharmaceutical compositions of the present invention are preferably presented for administration to humans in unit dosage forms known to those skilled in the art, such as tablets, capsules, pills, granules, sterile parenteral solutions or suspensions, and oral solutions or suspensions and the like, containing suitable quantities of the active ingredients. Examples are given in the following paragraphs. One or more ingredients, other than riboflavin, an effector of the urea cycle, and selected amino acids, may be present as diluents, carriers, or excipients in any composition of the present invention.

For intravenous administration, the pharmaceutical composition can be formulated as an intravenous solution of sodium salts in water suitable for injection.

For oral administration, either solid or fluid unit dosage forms can be prepared. Formulation can be as a tablet, capsule, powder, spirit, or elixir, among others.

Fluid unit dosage forms for oral administration such as in syrups, elixirs and suspensions can be prepared wherein each teaspoonful of composition contains a predetermined amount of active ingredients for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredients, depending on the form and concentration used, can be either suspended or dissolved in the vehicle. In preparing solutions, the water-soluble active ingredients can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

Powders are prepared quite simply by comminuting the active ingredients to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of the active ingredients with an acceptable vegetable oil, light liquid petolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate, and the like. The powder mixture can be granulated by wetting with a binder such as corn syrup, gelatin solution, methylcellulose solution or acacia mucilage and forcing through a screen. As an alternative to granulating, the powder mixture can be slugged, i.e. run through a tablet machine and the resultant imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and a polish coating of carnauba wax.

For intranasal instillation, a fluid unit dosage form is prepared using active ingredients and a suitable pharmaceutical vehicle, preferably P.F. water, wherein a dry powder can be formulated when insufflation is the administration of choice.

For the use as aerosols, the active ingredients can be packaged in a pressurized aerosol container together with a gaseous or liquified propellant, for example, dichlorofluoromethane, carbon dioxide, nitrogen, propane, and the like, with the usual adjuvants such as cosolvents and wetting agents as necessary or desirable.

One aspect of the present invention is to provide a pharmaceutically acceptable agent for the alleviation of the symptoms of fatigue and weakness associated with cancer and cancer chemotherapy, comprising a therapeutically effective amount of riboflavin, an effector of the urea cycle, and one or more amino acids selected from a group of essential and non-essential amino acids, wherein the latter two constituents are in free form or pharmacologically acceptable salts. The concentration of riboflavin in the composition is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL. As a result, the composition has a pH of about 6.0 to about 7.0.

A preferred composition consists of the six amino acids, alanine, glycine, serine, taurine, threonine, and valine; an effector of the urea cycle selected from L-arginine, L-ornithine, and L-citrulline; riboflavin; and a pharmaceutically acceptable diluent.

Another aspect of the present invention is to provide a pharmaceutically acceptable agent for the alleviation of the symptoms of fatigue and weakness associated with cancer and cancer chemotherapy, comprising a therapeutically effective amount of riboflavin, an effector of the urea cycle, and one or more amino acids selected from a group of essential and non-essential amino acids, and 3-phenylacetylamino-2,6-piperidinedione or one or more metabolites of 3-phenylacetylamino-2,6-piperidinedione. The concentration of riboflavin in the composition is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL.

A preferred composition consists of 0.01-10 wt % riboflavin, 1-15 wt % arginine, 1-15 wt % ornithine, 1-15 wt % alanine, 1-15 wt % glycine, 1-15 wt % serine, 1-15 wt % threonine, 1-15 wt % valine, and 25-75 wt % 3-phenylacetylamino-2,6-piperidinedione or 25-75 wt % phenylacetylglutamine and/or 25-75 wt % phenylacetylisoglutamine. Preferably, 3-phenylacetylamino-2,6-piperidinedione, phenylacetylglutamine and phenylacetylisoglutamine are present in L- or D-stereoisomeric form, or racemic mixture form.

A still another aspect of the present invention is to provide a pharmaceutically acceptable agent for the alleviation of the symptoms of fatigue and weakness associated with cancer and cancer chemotherapy cytotoxicity, comprising a therapeutically effective amount of riboflavin, an effector of the urea cycle, and one or more amino acids selected from a group of essential and non-essential amino acids, and sodium phenylbutyrate. The concentration of riboflavin in the composition is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL.

A preferred composition consists of 0.01-10 wt % riboflavin, 1-15 wt % arginine, 1-15 wt % ornithine, 1-15 wt % alanine, 1-15 wt % glycine, 1-15 wt % serine, 1-15 wt % threonine, 1-15 wt % valine, and 25-75 wt % sodium phenylbutyrate.

Optionally, all compositions according to the present invention can include other agents, such as buffering compounds, glucose, or other sugars, preservatives, and the like suitable for use in pharmaceutical compositions prepared for intravenous administration, as are known in the art.

B. Method of Administration of Pharmaceutical Compositions

A pharmaceutical composition of the present invention can be administered via the appropriate route for its formulation as described above. The pharmaceutical compositions of the present invention are preferrably administered intravenously. If it is formulated as an intravenous solution, it shall be administered through a single-channel infusion pump and IV catheter. The catheter will be a single-lumen Broviac, Groshong, or equivalent. The regimen for injections will vary depending upon age and the concentration of arginine in their plasma, as outlined below. Methods of intravenous administration are widely known in the art.

1) Regimen for Patients Older than 16 Years of Age

Day 1

Perform skin tests with 0.2 mL of the injection. If the skin test is negative, thirty minutes after the skin test, administer 10 mL of injection at 50 mL/h. Check the blood pressure and heart rate before and after completion of the injection.

Thirty minutes later, administer 50 mL of the injection at a rate of 100 mL/h. Check the blood pressure and heart rate at the beginning of the injection and every 15 minutes during the course of the injection.

If no side effects are observed after the administration of 50 mL of the injection, thirty-minutes later administer 440 mL of the requisite injection at 250 mL/h (the remainder of the 500 mL IV bag). Check the blood pressure and heart rate of the patient before the injection, 15 minutes after the beginning of the injection, one hour after beginning the injection, immediately after completion of the injection, and 30 minutes after completion of the injection.

Day 2

If no side effects have been noticed after the completion of Day 1, administer 500 mL of the requisite injection at 250 mL/h. Check the blood pressure and heart rate before the injection, every hour during the injection, and 30 minutes after completion of the injection.

Proceed with the administration of an additional 500 mL of the injection at a rate of 250 mL/h, unless otherwise modified by the treating physician. Check the blood pressure and heart rate before the injection, every hour during the injection, and 30 minutes after completion of the injection.

Day 3 and All Following Days

If no side effects have been noticed following the administration of 1000 mL of solution on Day 2, administer 1000 mL of the injection at a rate of 250 mL/h. Check the blood pressure and heart rate of the patient before the injection, after 1 hour from the beginning of the injection, immediately following completion of the injection, and 30 minutes after the completion of the injection.

2) Regimen for Patients Between 4 and 16 Years of Age

Day 1

Perform skin tests on the patient with 0.2 mL of the appropriate injection. If the skin test is negative, thirty minutes after the test, administer 10 mL of the injection at a rate of 50 mL/h. Check the blood pressure and heart rate both before and after the completion of the injection.

Thirty minutes later, administer 50 mL of the appropriate injection at a flow rate of 100 mL/h. Check the blood pressure and heart rate of the patient at the beginning of the injection and every 15 minutes during the course of the injection.

If no side effects were observed after the administration of 50 mL of solution, thirty minutes later, administer 440 µL of the injection at a flow rate of between 100 mL/h and 200 mL/h, depending upon the patient's age and tolerance according to the chart below. Check the blood pressure and heart rate before the injection, 15 minutes after the beginning of the injection, 1 hour after initiating the injection, immediately after completion of the injection, and 30 minutes after completion of the injection.

| Age of Patient (years) | Flow Rate of Administration of Solution (mL/h) |
|---|---|
| 4-7 | 100 |
| 7-10 | 150 |
| 10-16 | 200 |

Day 2

If no side effects were noticed following Day 1, as described above, administer 500 mL of the appropriate injection at the flow rate recommended for the patient's age, as shown in the chart above. Check the blood pressure and heart rate before the injection, every hour during the injection, and 30 minutes following the completion of the injection.

For patients older than 10 years of age, proceed with the administration of an additional 500 mL of the appropriate injection at 200 mL/h, but only if ordered by the treating physician. Check the blood pressure and heart rate at the same interval as after the injection of the first 500 mL.

Day 3 and Following Days

If no side effects were noticed after the administration of 500 nL of the solution on day 2, administer 500 mL or 1000 mL of the appropriate injection, if ordered by the treating physician, at the flow rate recommended for the patient's age. Check the blood pressure and heart rate before the injection, after 1 hour from the initiation of the injection, immediately after the completion of the injection, and 30 minutes following the completion of the injection.

The treatment regimen described above is useful in the treatment of patients suffering from a variety of neoplastic disease, including cancers, both of the hard tissue and soft tissue types, as well as malignant and benign tumors. In particular, neoplastic diseases that are advantageously susceptible to treatment using the disclosed treatment regimen of this invention include carcinoma of the adrenal gland, carcinoma of the bladder, carcinoma of the breast, high grade glioma, glioblastoma multiforme, astrocytoma including anaplastic and low grade astrocytoma, brain stem glioma, primitive neuroectodermal tumors including medulloblastoma and pinealoblastoma, rhabdoid tumor of the central nervous system, oligodendroglioma, mixed glioma, neurofibroma, schwannoma, visual pathway glioma, ependymoma, germ cell tumors, meningioma, carcinoma of the colon and rectum, carcinoma of the esophagus, primary and metastatic liver cancer, carcinoma of the head and neck, adenocarcinoma of the lung, large cell undifferentiated carcinoma of the lung, bronchio-alveolar carcinoma of the lung, squamous cell carcinoma of the lung, non-small cell carcinoma of the lung, non-Hodgkin's lymphomas, chronic leukemias, mesothelioma, malignant melanoma, malignant fibrous histiocytoma, multiple myeloma, neuroblastoma, neuroendocrine tumros, carcinoma of the ovary, carcinoma of the pancreas, primitive neuroectodermal tumors outside the central nervous system, adenocarcinoma of the prostate, carcinoma of the kidney, sarcomas, carcinoma of the small intestine, carcinoma of the stomach, carcinoma of the uterus, carcinoma of the vulva, and carcinoma of an unknown primary. Additionally, the described treatment regimen is useful for alleviation of symptoms and toxic effects associated with standard chemotherapeutic regimens, as well as for restoring patient nutritional status. The duration of the therapeutic regime may be for only as much time as is required in order to alleviate the symptoms and side-effects of the cancer chemotherapy treatment. Alternatively, the duration of the therapeutic administration may be for any or all of the length of time following initial cancer treatment.

A further aspect of the present invention is to provide a method for alleviating or reducing fatigue and weakness of a patient associated with cancer and cancer chemotherapy. This method comprises the step of administering to the patient with a composition comprising riboflavin; an effector of the urea cycle selected from the group consisting of arginine, ornithine, citrulline, and mixture thereof; the amino acids alanine, glycine, serine, taurine, threonine, and valine; and a suitable solvent, diluent, excipient, or carrier. The concentration of riboflavin in the composition is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL. The composition can be preferably administered enterally or parenterally. Alternatively, the composition can be administered intravenously.

Preferably, this method can further comprise the step of co-administering to the patient with an effective amount of 3-phenylacetylamino-2,6-piperidinedione or at least one metabolite of 3-phenylacetylamino-2,6-piperidinedione or sodium phenylbutyrate.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following case histories illustrate successful methods of treatment employing AVA or AVB for the treatment of adenocarcinoma, non-Hodgkin's lymphoma, and metastatic transitional cell carcinoma.

EXAMPLE 1

Treatment of 53-Year Old Female Diagnosed with Adenocarcinoma of the Colon using AVA Formulation A composition comprising a sterile solution of six amino acids, L-arginine, and riboflavin, hereinafter referred to as AVA was tested for its ability to alleviate the symptoms of cancer chemotherapy and improve the nutritional status of a middle-aged cancer patient.

A fifty-three-year old Caucasian female, diagnosed with adenocarcinoma of the sigmoid colon was treated surgically by lower anterior resection and anastomosis between the descending colon and the rectum. Following recovery, she was started on a daily intravenous administration of AVA. This was followed closely by the initiation of a combination chemotherapy regimen involving intravenous infusions of methotrexate and 5-fluorouracil (5-FU). Following weekly administration of the chemotherapy cocktail for fifty-two weeks, the chemotherapy was discontinued, and shortly thereafter the AVA treatment was discontinued.

Following the first two weeks of chemotherapy treatment in combination with AVA treatment, the patient reported a recovery of her strength and did not experience the side effects typically associated with this treatment (tiredness, loss of appetite, mucositis, diarrhea, and myelosuppression). Over the next year of treatment, the patient had regained the weight lost during the year previous to diagnosis. Follow-up evaluations involving physical examination, blood count, biochemical profile, urinalysis, electrolyte level tests, and appropriate CT scans indicated no cancer recurrence.

The results of the intravenous AVA treatment in conjunction with standard cancer chemotherapy regimens indicate that the pharmaceutical formulations of the present invention, and variations thereon, can act to alleviate the symptoms and improve the nutritional status of cancer patients.

EXAMPLE 2

Treatment of 70-Year Old Female Diagnosed with Ductal Adenocarcinoma of the Breast using AVA Formulation A composition comprising a sterile solution of six amino acids, L-arginine, and riboflavin, hereinafter referred to as AVA was tested for its ability to alleviate the symptoms of cancer chemotherapy and improve the nutritional status of an elderly cancer patient.

A 70-year old Caucasian female, diagnosed with infiltrating ductal adenocarcinoma, was treated surgically, then started on a nine-cycle chemotherapy regime using a cocktail of Cytoxan (cyclophosphamide), methotrexate, and 5-FU, followed by two months of radiation therapy in conjunction with tamoxifen. The tamoxifen treatment was discontinued due to side effects. Two years later, the patient developed a cancerous nodule behind the left axilla, confirmed by biopsy. Immediately thereafter, the patient was started on Taxol and received twenty-one treatments, whereup CT analysis of the chest indicated three nodules in the lungs and one in the liver. The patient was then started on daily intravenous infusions of AVA. Two months later, she was started on tamoxifen hormonal treatment, which continued for fourteen months. After discontinuation of tamoxifen, combination chemotherapy was begun with weekly injections of methotrexate and 5-FU in combination with Aromasin.

During the course of the current treatment, the patient showed a gradual improvement in her condition and exhibited an absence of fatigue and weakness and a gradual weight recovery. Follow-up evaluations involving physical examination, blood count, biochemical profile, urinalysis, electrolyte level tests, and CT scans of the chest and abdomen indicated two pulmonary and one liver lesion; the third pulmonary nodule was no longer visible. Of the two pulmonary lesions, one of those still present was larger in size in comparison with the baselines studies, and the second was notably smaller, indicating a remission of two of the lesions.

The treatment with daily infusions of AVA in combination with a battery of chemotherapeutic agents has resulted in a decrease in the size, as well as the complete disappearance of tumors. In addition, symptoms such as substantial cytotoxicity and related side effects preventing utilization of a particular therapeutic agent were alleviated and the nutritional status of the cancer patient undergoing the extreme therapeutic regimen was notably improved.

The patient is continuing a maintenance treatment with AVA, phenylbutyrate sodium, methotrexate, 5-FU and Aromasin, and continues to show improvement.

EXAMPLE 3

Treatment of 52-Year Old Female Diagnosed with Non-Hodgkin's Lymphoma using AVA Formulation A composition comprising a sterile solution of six amino acids, L-arginine, and riboflavin, hereinafter referred to as AVA was tested for its ability to alleviate the symptoms of cancer chemotherapy and improve the nutritional status of an elderly cancer patient.

A 52-year-old Caucasian female, diagnosed with low-grade non-Hodgkin's lymphoma, was treated initially with CHOP (combination of Cyclophosphamide, Doxorubicin/hydroxydoxorubicin, and Vincristine along with the corticosteroid Prednisolone) chemotherapy for a period of six months. CT scans indicated no measurable disease. One year later, the low-grade non-Hodgkin's lymphoma had returned to the patient's neck, chest, abdomen and pelvis. Treatment was begun using daily intravenous infusions of AVA. The AVA infusions were continued for four months, during which time the patient reported no symptoms typical of the cytotoxicity expected from the chemotherapeutic regimen involved. Shortly afterwards, she began treatment involving subcutaneous injections of Intron-A. Five months later, chemotherapy with Cytoxan was begun, and was continued for five months. During this time, chemotherapy using Rituxan was begun, but soon discontinued.

EXAMPLE 4

Treatment of 72-Year-Old Female Diagnosed with Transitional Cell Carcinoma of the Bladder using AVB Formulation A composition comprising a sterile solution of six amino acids, L-ornithine, and riboflavin, hereinafter referred to as AVB was tested for its ability to alleviate the symptoms of cancer chemotherapy and improve the nutritional status of an elderly cancer patient.

A 72-year-old Caucasian female was diagnosed with transitional cell carcinoma, papillary and invasive, grade 3, within the bladder wall. Due to two lymph nodes out of two being positive for metastatic transitional cell carcinoma of the bladder, cystectomy was not persued. The patient underwent urinary diversion and ileal conduit to relieve voiding symptoms, but no radiation therapy or chemotherapy regimen was initiated. Shortly thereafter, the patient was started on intravenous infusions of AVB. One week later, she began combination chemotherapy with methotrexate and 5-FU, the latter of which was given intravenously once a week.

Almost immediately after the start of the AVB infusions, and during the course of the treatments, the patient reported good appetite and energy levels and tolerated the chemotherapy very well. After 11 months, treatment with AVB was discontinued. Follow-up evaluation with CT scans of the chest, abdomen and pelvis seven months after the initiation of treatment showed complete remission of the enlarged mediastinal lymph node. The CT scan also revealed a decrease in the size of the lymph nodes in the pelvis and abdomen, as well as in the size of the left and right adrenal glands.

All of the compositions disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A nutritional composition for alleviating or reducing fatigue and weakness associated with cancer and cancer chemotherapy comprising riboflavin; an effector of the urea cycle selected from the group consisting of arginine, ornithine, citrulline, and mixture thereof; the amino acids alanine, glycine, seine, taurine, threonine, and valine; a suitable solvent, diluent, excipient, or carrier; and one or more of phenylbutyrate, phenylisoglutamine or phenylglutamine, wherein the concentration of riboflavin is about 5 to about 300 mg/L, concentration of the effector of the urea cycle is about 2 to about 120 mg/mL, concentration of alanine is about 1 to about 90 mg/mL, concentration of glycine is about 1 to about 75 mg/mL, concentration of serine is about 1 to about 75 mg/mL, concentration of taurine is about 0.5 to about 30 mg/mL, concentration of threonine is about 1 to about 90 mg/mL, and concentration of valine is about 1 to about 50 mg/mL and said composition is devoid of the amino acids, glutamine, leucine, and tryptophan.

2. The nutritional composition of claim 1, wherein the composition comprises 25-75 wt % phenylacetylglutamine, phenylisoglutamine, phenylbutyrate or combination thereof.

3. The nutritional composition of claim 1, wherein phenylacetylglutamine, phenylisoglutamine or phenylbutyrate is present in L- or D-stereoisomeric form.

4. The nutritional composition of claim 1, wherein phenylacetylglutamine, phenylisoglutamine or phenylbutyrate is present in racemic mixture form.

5. The nutritional composition of claim 1, wherein the phenylglutamine is 3-phenylacetylamino-2,6-piperidinedione.

6. A method for alleviating or reducing fatigue and weakness of a patient associated with cancer and cancer chemotherapy, comprising the step of:
   administering to the patient with a composition comprising according to claim 1.

7. The method of claim 6 further comprising the step of co-administering to the patient an effective amount of 3-phenylacetylamino-2,6-piperidinedione.

8. The method of claim 6 further comprising the step of co-administering to the patient an effective amount phenylacetylglutamine, phenylacetylisoglutamine, phenylbutyrate or combinations thereof.

9. The method of claim 6 wherein the composition is administered enterally or parenterally.

10. The method of claim 6 wherein the composition is administered intravenously.

* * * * *

UNITED STATES PATENT AND TRADEMARK OFFICE
CERTIFICATE OF CORRECTION

PATENT NO. : 7,427,619 B2  
APPLICATION NO. : 11/108277  
DATED : September 23, 2008  
INVENTOR(S) : Stanislaw R. Burzynski Page 1 of 1

It is certified that error appears in the above-identified patent and that said Letters Patent is hereby corrected as shown below:

Column 16, Claim 1, line 6:    delete "seine" insert --serine--

Signed and Sealed this

Eleventh Day of November, 2008

JON W. DUDAS  
*Director of the United States Patent and Trademark Office*